United States Patent
Roux et al.

[11] Patent Number: 5,549,693
[45] Date of Patent: Aug. 27, 1996

[54] COTYLOIDAL PROSTHESES

[76] Inventors: Christiane Roux, 3 Chemin du Petit Mont Solu Noisy sur Ecole, 77123 Le Vaudoue; Michel Pequignot, 16 Villa Désiré Filleaud, 92140 Clamart, both of France

[21] Appl. No.: 258,827

[22] Filed: Jun. 13, 1994

[30] Foreign Application Priority Data

Jun. 17, 1993 [FR] France .................................. 93 07295

[51] Int. Cl.⁶ ........................................................ A61F 2/32
[52] U.S. Cl. .................... 623/22; 623/18; 623/23
[58] Field of Search ................... 623/18, 22, 23

[56] References Cited

U.S. PATENT DOCUMENTS

| | | |
|---|---|---|
| 4,408,360 | 10/1983 | Keller . |
| 4,676,798 | 6/1987 | Noiles ........................................ 623/22 |
| 4,784,662 | 11/1988 | Müller . |
| 4,969,910 | 11/1990 | Frey et al. . |
| 5,062,853 | 11/1991 | Forte .......................................... 623/22 |
| 5,092,898 | 3/1992 | Bekki et al. ............................... 623/22 |
| 5,263,988 | 11/1993 | Huebner .................................... 623/22 |

FOREIGN PATENT DOCUMENTS

| | | |
|---|---|---|
| 0051686 | 5/1982 | European Pat. Off. . |
| 0053794 | 6/1982 | European Pat. Off. . |
| 0226762 | 7/1987 | European Pat. Off. . |
| 0315795 | 5/1989 | European Pat. Off. . |
| 2225141 | 11/1974 | France . |
| 2626766 | 8/1989 | France . |
| 9215863 | 7/1993 | Germany . |
| 1472311 | 5/1977 | United Kingdom . |
| 1472312 | 5/1977 | United Kingdom . |

*Primary Examiner*—Robert A. H. Clarke
*Attorney, Agent, or Firm*—Young & Thompson

[57] ABSTRACT

A prosthesis has a ceramic part to cooperate with a spherical head. This ceramic part is a ring whose inside surface is part of a sphere. The prosthesis is suitable for coxofemoral joints.

13 Claims, 1 Drawing Sheet

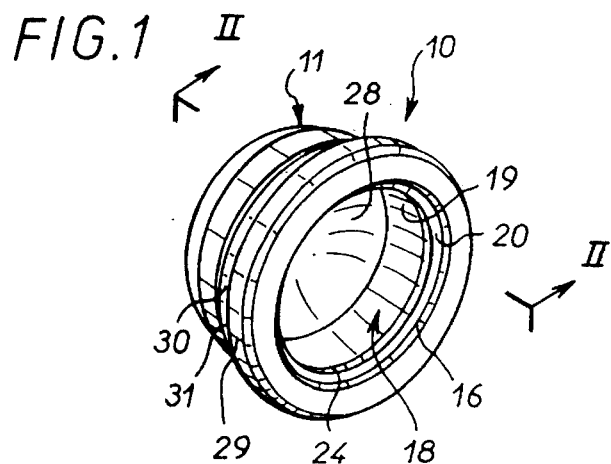
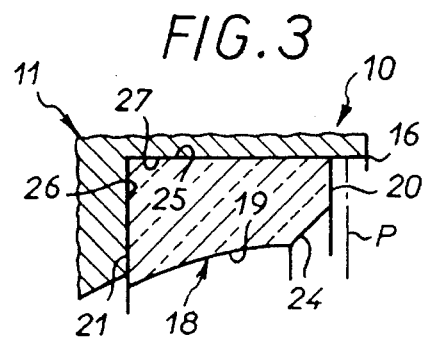
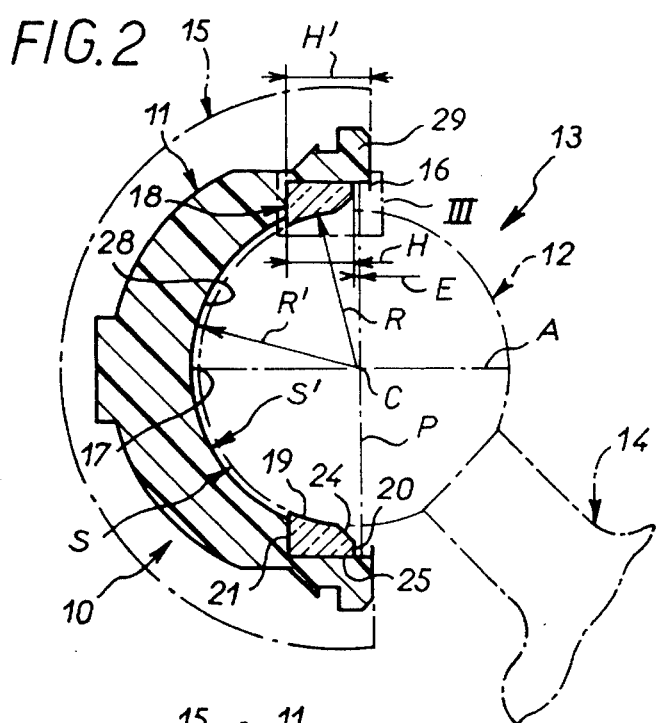
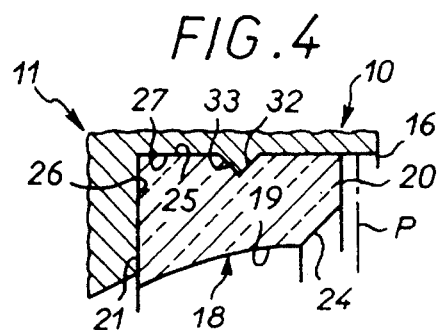
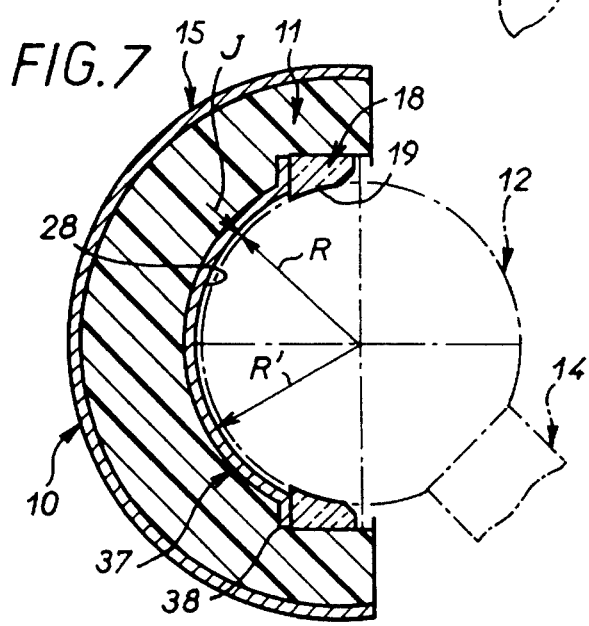
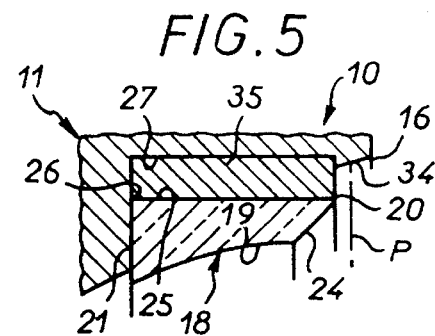
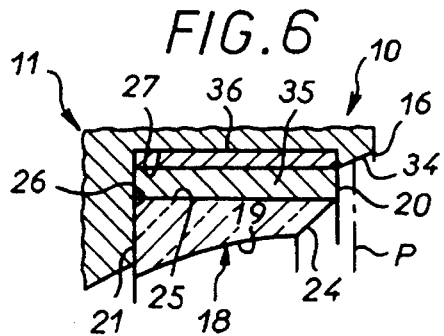

COTYLOIDAL PROSTHESES

BACKGROUND OF THE INVENTION

1. Field of the Invention

The present invention is generally concerned with cotyloidal prostheses and is more particularly, but not necessarily exclusively, concerned with the situation in which a cotyloidal prosthesis is used to replace a coxofemoral joint.

2. Description of the Prior Art

Prior art coxofemoral joint prostheses have two complementary parts: namely a hemispherical cup or cotyle adapted to be fixed directly or indirectly by means of a fixing member to the cotyloid cavity of the iliac bone of the patient and a ball-shaped spherical head at the end of a stem adapted to be inserted into the MNO of the patient.

Given the excellent coefficient of friction of a ceramic material such as an alumina ceramic and the biocompatibility of such materials with bone tissue, it has previously been proposed to make both the spherical head and the cup from ceramic.

Even though, with reference to the spherical head, machining a ceramic ball is relatively simple, and consequently feasible at a relatively acceptable cost, this is by no means true of the cup.

Given the accuracy required for perfect congruence with the associated spherical head and given that at present this is a relatively massive component made in one piece, the cost of a ceramic cup is particularly high.

The accuracy of machining required for the cup leads to the use of techniques employed in optics, in this instance abrasive machining using progressively finer abrasives.

Finish machining of the spherical head and the cup is achieved by mutual abrasion, requiring precise pairing of these components, with resulting considerable difficulties in terms of storage and use.

Most coxofemoral joint prostheses are for older patients, in whom there is a particular tendency for eventual detachment of the cup when it is made from ceramic, this being attributable, for example, to poor attachment of the ceramic to the bone tissue in this case. For this reason, ceramic cups are at present usually employed only for younger patients whose bone tissue seems better able to accommodate this material, probably because the damping of normal impacts, such as those occasioned on walking, is better in these patients.

In older patients the cup is therefore usually made from a synthetic material at present, to be more precise from high-density polyethylene, whereas the spherical head is preferably made of ceramic.

Apart from the inevitable production of polyethylene debris which is currently suspected of causing bone damage, coxofemoral joint prostheses including a synthetic material cup have the drawback of a shorter service life than those in which the cup is made from ceramic.

Various studies have shown that, regardless of the materials from which they are made, the spherical head moves progressively deeper into the cup, partly because of cold flow of the synthetic material of the latter and partly because the spherical head wears away the synthetic material.

Incidentally, this is the reason why coxofemoral joint prostheses using a ceramic-ceramic rubbing pair, i.e. in which the cup and the spherical head are both made of ceramic, are increasingly attracting interest, given the requirement for a long service life in younger patients.

In these devices there is no cold flow and there is virtually no wear.

Additionally, there is no risk of production of polyethylene debris.

A general object of the present invention is a cotyloidal prosthesis which, by virtue of improvements to the use of a ceramic-ceramic rubbing pair, provides in a very simple manner an advantageous compromise between coxofemoral joint prostheses with a ceramic cup and those with a synthetic material cup, and which additionally has further advantages.

It is based on the observation that, in bipeds, the parts of the bone components concerned, namely the cotyloid cavity and the femoral head, which are actually loaded are in practise usually restricted to a small portion of the joint crescent, substantially equivalent to the roof only of the cotyloid cavity.

Gravity and the locomotor function cause the pressure of the head of the femur on the cotyloid cavity to be greater at its roof.

The cotyloidal prosthesis of the invention is particularly suitable for a coxofemoral joint.

SUMMARY OF THE INVENTION

The present invention consists in a cotyloidal prosthesis, in particular for coxofemoral joints, of the kind including a ceramic part adapted to cooperate with a spherical head, said ceramic part comprising a ring having a part-spherical inside surface, that is this surface is part of a sphere.

The invention thus divides functions between a ceramic internal part, in this instance the ring, whose function is to cooperate with the spherical head to make the joint, and an external part such as a synthetic material cup whose only function is to connect the ring to the cotyloid cavity, being fixed to the latter in the usual way and either directly, for example by cementing it in place, or indirectly, for example by means of a metal fixing member.

However, by restricting the ceramic part to the active, i.e. functional, portion, all the advantages of using ceramic are retained with a substantial cost reduction.

Extending to only part of the depth of the synthetic material cup, the ceramic ring of the invention has a height and a thickness which are significantly reduced as compared with those of a cup.

The quantity of ceramic used is therefore reduced very substantially, by a factor of 3 to 6, for example. Also, the cost of machining and polishing the ring is reduced as compared with a cup.

If a fixing member is used the presence of the ceramic ring has the advantage of providing as much room as is required on the external surface of the synthetic material cup for recesses to accommodate the fixing means for attaching the fixing member to the cotyloid cavity, with no risk that the resulting localized thinning of the cup at these locations leading, through cold flow and wear, to direct rubbing of the spherical head on the fixing means, as could happen if there were no such ring.

Given its reduced thickness, which provides the necessary room in the radial direction, the ceramic ring of the invention is advantageously externally hooped to increase its mechanical strength and in particular its resistance to impact and bursting.

The radial stresses due to hooping effectively oppose the propagation of microcracks, such as the cracks that can occur in ceramics, especially due to the action of alternating stresses and/or in the presence of a wetting liquid, as in the case of a joint prosthesis.

Given its relatively small dimensions, it is feasible to make the ceramic ring from a single crystal, cut on the appropriate axis, rather than by sintering, which would eliminate any risk of grain separation and the consequences thereof inherent to manufacture by sintering.

Given its thinness, it is also feasible, without increasing the overall dimensions, to surround the ceramic ring with a ring of elastic material to enhance the damping properties of the prosthesis as a whole.

The features and advantages of the invention emerge from the following description given by way of example with reference to the appended diagrammatic drawings.

BRIEF DESCRIPTION OF THE DRAWINGS

FIG. 1 is a perspective view of a cotyloidal prosthesis in accordance with the invention.

FIG. 2 is a view of the prosthesis to a larger scale and in axial section on the line II—II in FIG. 1.

FIG. 3 shows to a larger scale the part of FIG. 2 indicated by a box III in FIG. 2.

FIG. 4 is a partial view in axial section analogous to FIG. 3 for a first modified embodiment;

FIG. 5 is a partial view in axial section analogous to FIG. 3 for a second modified embodiment;

FIG. 6 is a partial view in axial section analogous to FIG. 3 for a third modified embodiment;

FIG. 7 is a view in axial section, analogous to FIG. 2, and relating to a further embodiment of the invention.

DETAILED DESCRIPTION OF THE PREFERRED EMBODIMENTS

Referring to the figures, the cotyloidal prosthesis 10 in accordance with the invention includes, in the known manner, a synthetic material cup 11 adapted to be implanted in a cotyloid cavity (not shown) and to cooperate, internally, with a spherical head 12 shown in chain-dotted outline in FIG. 2.

The resulting joint prosthesis 13 is for replacing a coxofemoral joint, for example.

The cotyloid cavity is in this case part of the ilium of the patient. The spherical head 12 is at the end of a stem 14 inserted in and fastened to the femur of the patient.

The spherical head 12 is a ceramic ball, for example an alumina ceramic ball. It is appropriately fastened to the stem 14, for example by means of a conical interference fit, and the stem 14 is made from metal, for example.

The cup 11 is made from high-density polyethylene, for example, and for fixing it to the cotyloid cavity it is associated with a fixing member 15 disposed around it, as shown diagrammatically in chain-dotted outline in FIG. 2, and which is also generally cup-shaped. It is clipped into this member, for example.

The fixing member 15 is made of metal, for example.

It is usually fastened to the cotyloid cavity by screwing it in, by driving it in or by cementing it in place.

The foregoing provisions are well known in themselves and as they are not directly relevant to the present invention they are not described in further detail here.

Also in the known manner, the cotyloidal prosthesis 10 includes a ceramic part 18 to cooperate with the spherical head 12.

In accordance with the invention, this ceramic part 18 is a ring whose inside surface 19 is part of a sphere S.

The radius R of the sphere S is naturally equal to that of the spherical head 12.

In other words, the sphere S is complementary to the spherical head 12.

The sphere S has a center C.

In the embodiments shown the ring constituting the ceramic part 18 is carried by the cup 11.

It is disposed in the cup 11, near its opening.

The height H of the ring constituting the ceramic part 18, measured parallel to its axis A, is preferably at most equal to half the radius R of the sphere S.

This height H is between one-third and half the radius R, for example.

In any event, the ring constituting the ceramic part 18 extends over only a fraction of the depth of the cup 11, measured between its opening 16 and its inner end 17.

In the embodiments shown the front surface 20 and the rear surface 21 of the ring constituting the ceramic part 18 are in two parallel planes perpendicular to the axis A.

To be more precise, in these embodiments the front surface 20 of the ring constituting the ceramic part 18 lies in a plane which is slightly set back relative to the equatorial plane P of the sphere S perpendicular to the axis A, between this equatorial plane P and the far end 19 of the cup 11.

In practise, the corresponding offset E is small.

It is deliberately exaggerated in the figures so that it can been seen clearly.

In the embodiments shown, the edge of the ring constituting the ceramic part 18 is formed with a bevel 24 where its inside surface 19 joins its front surface 20 to prevent weakening at this point by stress concentration.

The corresponding rubbing surface area is reduced commensurately.

The size of the bevel 24 is deliberately exaggerated in the figures.

In the embodiments shown, the outside surface 25 of the ring constituting the ceramic part 18 is cylindrical, with generatrices parallel to the axis A.

The ring constituting the ceramic part 18 is preferably made from alumina ceramic.

It is sintered, for example, using the isostatic compression or high isostatic pressure (HIP) treatment which is standard in this art.

In the embodiment shown in FIGS. 1 to 3, the outside surface 23 of the ring constituting the ceramic part 18 is simply force-fitted into the cup 11.

For this purpose, the cup 11 has a cylindrical bearing surface 27 on its inside, extending from its opening 16 to a transverse shoulder 26.

In the embodiments shown, the height H' of this cylindrical bearing surface 27 is slightly greater than that H of the ring constituting the ceramic part 18 with the result that the front surface 20 of the latter is set back relative to the opening 16 of the cup 11.

Starting from the ring constituting the ceramic part 18, and therefore from the transverse shoulder 26, the inside surface 28 of the cup 11 is preferably spaced from the sphere S of which the inside surface 19 of the ring constituting the ceramic part 18 is part.

In the embodiment shown the inside surface 28 of the cup 11 is part of a sphere S' concentric with the sphere S and the diameter R' of the sphere S' is greater than that R of the sphere S.

In the embodiments shown the cup 11 has an annular rim 29 on its exterior, in line with its opening 16.

In the embodiments shown in FIGS. 4 to 6 clipping means are provided between the cup 11 and the ring constituting the ceramic part 18.

Referring to FIG. 4, for example, the ring constituting the ceramic part 18 has an annular groove 32 recessed into its external surface 25 and the cup 11 has a complementary annular bead 33 projecting from its cylindrical bearing surface 27.

In the embodiment shown the groove 32 and the bead 33 have a triangular profile in transverse cross-section.

Alternatively, as shown in FIGS. 5 and 6, the cup 11 has an annular bead 34 with a frustoconical outside surface projecting from its cylindrical bearing surface 27, starting from its opening 16, which clips over the ring constituting the ceramic part 18.

In the embodiment shown in FIG. 5 the ring constituting the ceramic part 18 is hooped on the outside and over all of its height by a shrink-fit band 35.

The band 35 is in practise made of metal.

For example, it is made from titanium alloy, from a low-carbon stainless steel or from a stellite type alloy, all of which materials have the advantage of being biocompatible.

In the embodiment shown in FIG. 6 the ring constituting the ceramic part 18 is further surrounded over its entire height by a ring 36 of elastic, for example elastomer, material disposed radially between it and the cup 11.

In the embodiment shown in FIG. 7 the synthetic material cup 11 is lined with a metal cup 37 preferably in contact with it at all points and intended to prevent any cold flow of the cup 11.

The cup 37 is made of titanium, for example, and its thickness is a few tenths of a millimeter.

In the embodiment shown it has a flange 38 projecting radially outwards along its free edge which fits under the ceramic part 18, between the latter and the corresponding shoulder of the synthetic material cup 11.

Otherwise, the design is similar to those previously described.

In particular, there remains in service a radial clearance J between the spherical head 12 and the cup 37.

In other words, the inside surface 28 of the cup 11 is in this case to be regarded as formed by the inside surface of the cup 27.

The present invention is naturally not limited to the embodiments described and shown, but encompasses any variant execution and/or combination of the various components thereof.

In particular, although the synthetic material cup has benefits of its own, in particular its damping capability and the ease with which it provides the necessary adaptation between the ring constituting the ceramic part and the external fixing member, this ring can be carried directly by the fixing member, being directly hooped by the latter.

Also, the ceramic used is not necessarily the alumina ceramic specifically mentioned.

It can equally well be zirconium ceramic, silicon nitride ceramic or, more generally, any ceramic material that can be sintered at high temperature.

There is claimed:

1. Cotyloidal prosthesis, in particular for coxofemoral joints, comprising cup means having a contact surface for ball-and-socket contact with a ceramic spherical head, said cup means including a ceramic socket ring having a part-spherical inside surface defining said contact surface of said cup means, said cup means further comprising a plastic material cup member having an opening for introducing the part-spherical head, said cup member carrying said ceramic socket ring near the opening of the cup member, further comprising a metal liner lining said plastic material cup member, said metal lining not defining any part of said contact surface of said cup means.

2. Cotyloidal prosthesis according to claim 1 wherein said cup member has an inner surface radially outerwardly spaced from a sphere defined by said part-spherical inner surface of said ceramic socket ring.

3. Cotyloidal prosthesis according to claim 2 wherein said cup member has an inner surface which is also part-spherical, the radius of the part-spherical surface of said cup member being greater than that of the part-spherical surface of said ceramic socket ring.

4. Cotyloidal prosthesis assembly according to claim 3 and further comprising a fixing member surrounding and secured to the cup means of the cotyloidal prosthesis.

5. Cotyloidal prosthesis according to claim 1 further comprising an elastic material ring interposed between said cup member and said ceramic socket ring for enhancing damping properties of the prosthesis.

6. Cotyloidal prosthesis according to claim 1 wherein said ceramic socket part is in force-fit engagement with the plastic material cup.

7. Cotyloidal prosthesis according to claim 1 further comprising clipping means disposed between said plastic material cup member and said ceramic socket part.

8. Cotyloidal prosthesis, in particular for coxofemoral joints, comprising cup means having a contact surface for ball-and-socket contact with a ceramic spherical head, said cup means including a ceramic socket ring having a part-spherical inside surface defining said contact surface of said cup means, said cup means having an opening for introducing the part-spherical head, said ceramic socket ring having a front surface lying in a plane slightly set back relative to an equatorial plane of a sphere defined by the part-spherical inside surface, such that the ceramic socket ring lies entirely to one side of the equatorial plane remote from said opening.

9. Cotyloidal prosthesis according to claim 8 wherein said ceramic socket ring has an axis, the height of said ceramic socket ring, measured parallel to the axis, being at most equal to one-half the radius of a sphere defined by the part-spherical inside surface.

10. Cotyloidal prosthesis according to claim 9 wherein the height of said ceramic socket ring is between one-third and one-half the radius of the sphere defined by the part-spherical inside surface.

11. Cotyloidal prosthesis according to claim 8 wherein said ceramic socket part has front and rear surfaces lying in spaced parallel planes.

12. Cotyloidal prosthesis according to claim 8 wherein said ceramic socket ring has a cylindrical outer surface.

13. Cotyloidal prosthesis according to claim 8 wherein said ceramic socket ring has a cylindrical outer surface, and a hooping band bears along substantially the entire height of the cylindrical outer surface of the ceramic socket ring to increase the mechanical strength of the ceramic socket ring.

* * * * *